(12) United States Patent
Weinberg et al.

(10) Patent No.: US 10,627,461 B2
(45) Date of Patent: Apr. 21, 2020

(54) METHOD AND APPARATUS FOR IMAGE-DIRECTED NERVE GROWTH

(71) Applicant: WEINBERG MEDICAL PHYSICS LLC, Bethesda, MD (US)

(72) Inventors: Irving N. Weinberg, Bethesda, MD (US); Lamar Odell Mair, Washington, DC (US); Randolph Nudo, Lawrence, KS (US)

(73) Assignee: WEINBERG MEDICAL PHYSICS INC

(*) Notice: Subject to any disclaimer, the term of this patent is extended or adjusted under 35 U.S.C. 154(b) by 1115 days.

(21) Appl. No.: 14/874,857

(22) Filed: Oct. 5, 2015

(65) Prior Publication Data

US 2016/0096031 A1 Apr. 7, 2016

Related U.S. Application Data

(60) Provisional application No. 62/059,403, filed on Oct. 3, 2014.

(51) Int. Cl.
*A61N 2/00* (2006.01)
*G01R 33/28* (2006.01)
*A61N 1/40* (2006.01)

(52) U.S. Cl.
CPC .............. *G01R 33/288* (2013.01); *A61N 1/40* (2013.01); *A61N 2/00* (2013.01)

(58) Field of Classification Search
CPC .................................................. A61N 2/00–12
See application file for complete search history.

(56) References Cited

U.S. PATENT DOCUMENTS

| | | | | |
|---|---|---|---|---|
| 6,132,360 A | * | 10/2000 | Halpern | A61N 2/00 128/898 |
| 8,154,286 B2 | | 4/2012 | Weinberg | |
| 8,466,680 B2 | | 6/2013 | Weinberg et al. | |
| 2013/0046169 A1 | | 2/2013 | Weinberg et al. | |
| 2014/0135680 A1 | * | 5/2014 | Peyman | A61N 5/062 604/20 |

OTHER PUBLICATIONS

Fan et al.; Flexible triboelectric generator; Nano Energy; Mar. 2012; pp. 328-334; vol. 1, No. 2.
McCaig; Nerve growth in a small applied elecric field and the effects of pharmacological agents on rate and orientation; Journal of Cell Science; Apr. 1, 1990; pp. 617-622; vol. 95.
Taylor et al.; A microfluidic culture platform for CNS axonal injury, regeneration and transport; Nature Methods; Jul. 21, 2005; pp. 599-605; vol. 2, No. 8.

* cited by examiner

*Primary Examiner* — Thaddeus B Cox
(74) *Attorney, Agent, or Firm* — Barnes & Thornburg LLP

(57) ABSTRACT

Disclosed embodiments are directed to promoting nerve growth through one or more mechanisms using an apparatus to rapidly change magnetic fields.

19 Claims, 1 Drawing Sheet

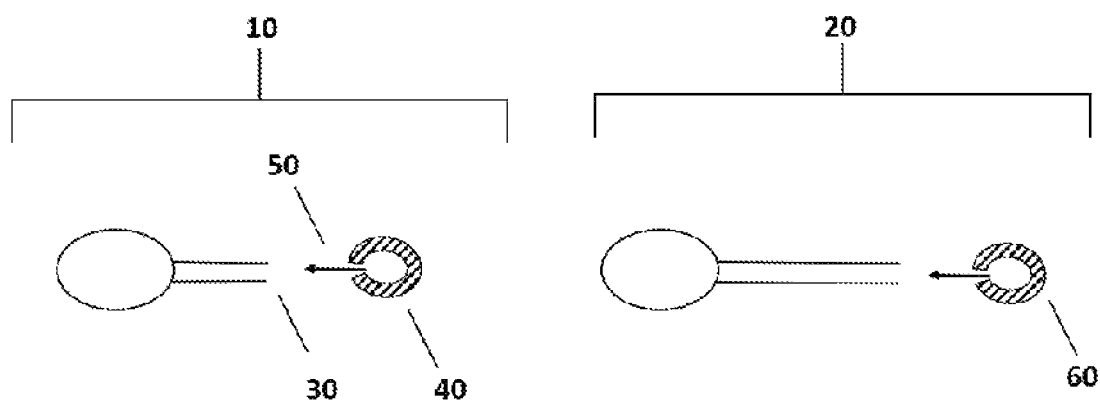

METHOD AND APPARATUS FOR IMAGE-DIRECTED NERVE GROWTH

CROSS REFERENCE

This application claims priority under 35 U.S.C. 119(e) to U.S. Provisional Patent Application 62/059,403 (incorporated by reference in its entirety) on Oct. 3, 2014, entitled "METHOD AND APPARATUS FOR IMAGE-DIRECTED NERVE GROWTH."

FIELD

Disclosed embodiments are directed to promoting nerve growth through one or more mechanisms using an apparatus to rapidly change magnetic fields.

SUMMARY

Disclosed embodiments perform preferentially-directed nerve growth through one or more mechanisms using an apparatus to rapidly change magnetic fields.

In accordance with at least one disclosed embodiment, magnetic gradients of the magnetic fields have very high magnitudes without causing discomfort to the subject.

In accordance with at least one disclosed embodiment, magnetic gradients have rise- and fall-times of less than 10 microseconds.

The apparatus also applies high magnetic fields rapidly to nerve tissues in order to induce electric fields that may assist in re-growing damaged nerve tracts, according, in part, to information provided by the MRI data.

The apparatus can also direct particles containing nerve-growth factors or other chemicals known to affect nerve growth to sites of damaged nerves and/or to intended sites of nerve growth, and to alter the position of such particles in time in order to obtain nerve growth over distances.

BRIEF DESCRIPTION OF THE FIGURES

The detailed description particularly refers to the accompanying figures in which:

FIG. 1 illustrates nerve growth through application of electric fields resulting from applying rapidly changing magnetic fields.

DETAILED DESCRIPTION

In some cases of disease, for example in Traumatic Brain Injury ("TBI") or spinal cord injury, nerve fibers are damaged or cut. In such cases, it could be helpful to induce regrowth of a nerve along a gap resulting from such a cut.

It is conventionally known that nerves may be induced to grow through the application of chemical factors, as taught by Anne M. Taylor et al in the publication entitled "A microfluidic culture platform for CNS axonal, regeneration and transport", in the journal Nature Methods Vol. 2, number 8, August 2005, pages 599-605 (hereby incorporated by reference in its entirety).

It is also known that electric fields can be used to induce nerve growth, for example as taught by Colin D. McCaig in the publication entitled "Nerve growth in a small applied electric field and the effects of pharmacologic agents on rate and orientation", published in 1990 in the Journal of Cell Science (volume 95, pages 617-622) (hereby incorporated by reference in its entirety).

Disclosed embodiments perform preferentially-directed nerve growth through one or more mechanisms using an apparatus to rapidly change magnetic fields. The configuration of the apparatus has been described in part in prior inventions by inventor Irving Weinberg, listed as U.S. Pat. Nos. 8,466,680 and 8,154,286, and related filed patent applications (by priority claim) to those patents (all incorporated by reference in their entireties). In accordance with those innovations, magnetic gradients have very high magnitudes without discomfort to the subject if the rise- and fall-times of the imposition were less than conventionally used (i.e., less than 10 microseconds).

The apparatus applies high magnetic fields to obtain high-resolution, Magnetic Resonance Images (MRI) of nerve assemblies without causing unpleasant bio-effects.

The apparatus also applies high magnetic fields rapidly to nerve tissues in order to induce electric fields that may assist in re-growing damaged nerve tracts, according, in part, to information provided by the MRI data.

The apparatus can also direct particles containing nerve-growth factors or other chemicals known to affect nerve growth to sites of damaged nerves and/or to intended sites of nerve growth, and to alter the position of such particles in time in order to obtain nerve growth over distances. A description of the image-guided particle manipulation apparatus invented by Weinberg is given in US patent application publication US 20130046169, which is entitled "MRI-guided nanoparticle cancer therapy apparatus and methodology" (hereby incorporated by reference in its entirety).

FIG. 1 provides an illustrative example of an application of electric fields in accordance with the disclosed apparatus and method. As shown in FIG. 1, panels 10 and 20, which correspond to application of an electric field(s) at sequential times. More specifically, as shown at panel 10, a nerve 15 has an axon that has been truncated 30.

A magnetizable particle 40 containing and eluting a growth factor 50 is directed near the nerve end 30, and is located in the direction that it is intended for the nerve end 30 to grow.

Alternatively particle 40 may contain a fuel cell, piezoelectric generator or electrically-active tribological segment with magnetizable sections that may be actuated with applied magnetic pulses. Accordingly, the particle 40 may apply an electric field 50 (the arrow included in FIG. 1 not necessarily indicating the polarity of the electric field). Such an electric field 50 may be provided, for example, utilizing conventionally known technology such as, for example, that disclosed in association with the small triboelectric generator described in the article "Flexible triboelectric generator!" by F-R Fan, Z-Q Tian, and Z L Wang, published in 2012 in the journal Nano Energy (vol. 1, pages 328-334) (incorporated by reference in its entirety). The triboelectric generator described by F-R Fan produces an electrical current by moving parts of the generator with respect to one another. In this invention, parts of the triboelectric generator are either made of, or attached to, ferromagnetic materials that are moved under the influence of magnetic pulses generated by the apparatus.

Turning to the time panel 20, which occurs after the application of the electric field, the nerve 15 has grown at its nerve end 30 and particle 60 has been moved in order to induce the nerve to continue to grow in the direction of particle 60.

It should be understood that there may be many particles 40, 60 and that they may be the same or different particles at effective to establish electric fields at different times.

It should be understood that components disclosed in the incorporated references interact in a manner that enables regrowth of nerves that have been previously damaged.

As a result, it should be understood that the presently disclosed functionality may be implemented in conjunction with those components under the control of one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments of the present invention. Such alternative storage devices should be considered equivalents.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

We claim:

1. A method of guiding growth of at least one nerve in a body part, the method comprising:
   sequentially moving at least one particle in order to continue to direct said growth in the direction of the particle,
   wherein motion of the at least one particle is caused by application of magnetic gradients,
   wherein the at least one particle is located and sequentially moved external to the at least one nerve.

2. The method of claim 1, further comprising generating at least one magnetic gradient using at least one coil under control of a control unit, so as to control the at least one coil to generate and transmit radio frequency energy into the body part to apply the magnetic gradients;
   detecting radio frequency energy received from the body part to obtain imaging data regarding the body part so as to perform magnetic resonance imaging of at least one nerve end in the body part;
   controlling the sequential movement of the at least one particle based on the obtained imaging data.

3. The method of claim 1, wherein the body part is the brain.

4. The method of claim 1, wherein the body part is the spinal cord.

5. The method of claim 1, wherein the body part is a peripheral nerve.

6. The method of claim 1, in which one or more of the applied magnetic gradients arises or falls in less than 10 microseconds so as not to cause discomfort.

7. The method of claim 1, wherein the at least one particle elutes at least one chemical that affects nerve growth.

8. The method of claim 1, wherein the application of magnetic gradients to move and/or concentrate the at least one particle is interleaved with the application of magnetic fields to visualize nerves or collections of nerves.

9. A method of guiding growth of at least one nerve in a body part, the method comprising:
   sequentially moving at least one particle in order to direct said growth,
   wherein motion of the at least one particle is caused by application of magnetic gradients,
   wherein the at least one particle generates an electric field in the vicinity of a nerve in order to affect nerve growth.

10. The method of claim 9, where the electric field is generated through a fuel-cell in the particle.

11. The method of claim 9, wherein the electric field is generated through motion of a piezoelectric generator that is actuated by application of a magnetic field external to the body part.

12. A method of guiding growth of at least one nerve in a body part, the method comprising:
   sequentially moving at least one particle in order to direct said growth,
   wherein motion of the at least one particle is caused by application of magnetic gradients,
   wherein the electric field is generated through motion of one or more portions of a tribological generator that is actuated by application of a magnetic field external to the body part.

13. The method of claim 12, further comprising generating at least one magnetic gradient using at least one coil under control of a control unit, so as to control the at least one coil to generate and transmit radio frequency energy into the body part to apply the magnetic gradients;
   detecting radio frequency energy received from the body part to obtain imaging data regarding the body part so as to perform magnetic resonance imaging of at least one nerve end in the body part;
   controlling the sequential movement of the at least one particle based on the obtained imaging data.

14. The method of claim 12, wherein the body part is the brain.

15. The method of claim 12, wherein the body part is the spinal cord.

16. The method of claim 12, wherein the body part is a peripheral nerve.

17. The method of claim 12, in which one or more of the applied magnetic gradients arises or falls in less than 10 microseconds so as not to cause discomfort.

18. The method of claim 12, wherein the at least one particle elutes at least one chemical that affects nerve growth.

19. The method of claim 12, wherein the application of magnetic gradients to move and/or concentrate the at least one particle is interleaved with the application of magnetic fields to visualize nerves or collections of nerves.

\* \* \* \* \*